(12) United States Patent
Metzner

(10) Patent No.: US 6,231,037 B1
(45) Date of Patent: May 15, 2001

(54) CASSETTE CLAMP FOR A MICROTOME

(75) Inventor: Rolf Metzner, Dossenheim (DE)

(73) Assignee: Leica Microsystems Nussloch GmbH, Nussloch (DE)

( * ) Notice: Subject to any disclaimer, the term of this patent is extended or adjusted under 35 U.S.C. 154(b) by 0 days.

(21) Appl. No.: 09/288,713

(22) Filed: Apr. 9, 1999

(30) Foreign Application Priority Data

Apr. 11, 1998 (DE) .............................. 198 16 375

(51) Int. Cl.$^7$ .................................................. B25B 1/00
(52) U.S. Cl. ....................................................... 269/254 CS
(58) Field of Search .................................. 269/237–239, 269/257, 203, 254 CS, 909; 83/915.5

(56) References Cited

U.S. PATENT DOCUMENTS

| | | | | |
|---|---|---|---|---|
| 1,745,379 | * | 2/1930 | Perry ............................. | 269/254 CS |
| 2,053,699 | * | 9/1936 | Coates ........................... | 269/254 CS |
| 3,552,733 | * | 1/1971 | Pickett .......................... | 269/216 |
| 3,802,691 | * | 4/1974 | White ............................ | 269/236 |
| 4,695,046 | * | 9/1987 | Berleth ......................... | 269/210 |
| 5,188,347 | * | 2/1993 | Hunnell et al. ............... | 269/258 |
| 5,673,905 | * | 10/1997 | Kiene ............................ | 269/238 |

FOREIGN PATENT DOCUMENTS

| | | |
|---|---|---|
| 30 40 217 | 10/1980 | (DE) . |
| 36 07 766 | 3/1986 | (DE) . |
| 43 33 118 | 3/1993 | (DE) . |

OTHER PUBLICATIONS

"LEICA RM 2145"; Leica Instruments GmbH; Jul. 1997; pp. 1–6.

* cited by examiner

*Primary Examiner*—Robert C. Watson
(74) *Attorney, Agent, or Firm*—Foley & Lardner

(57) ABSTRACT

A cassette clamp (1) for a microtome includes a base part (2) having fixed limit stops (3) and at least one pivotally mounted clamping jaw (5) biased by a spring (6) for receiving a cassette (4). The cassette (4) is clamped between the limit stops (3) and the clamping jaw (5) via the spring force. The clamping jaw (5) is connected to a pivot lever (7) that can be moved counter to the spring force from a cassette-clamping position into a cassette-exchange position. A first end (8a) of the spring (6) acts on the base part (2) and the second end (8b) of the spring (6) acts on the pivot lever (7). The pivot lever (7) is mounted on the base part (2) via a pivot axis (9) arranged between the first end (8a) of the spring and the second end (8b) of the spring. The spring (6) and the pivot lever (7) form a tilting clamp mechanism that can be activated by installing the cassette (4) when the cassette clamp (1) is in the cassette-exchange position.

3 Claims, 1 Drawing Sheet

CASSETTE CLAMP FOR A MICROTOME

BACKGROUND OF THE INVENTION

1. Field of the Invention

The invention relates to a cassette clamp for a microtome.

2. Description of the Related Art

Before specimens can be cut using a microtome, the specimens must be made stable. To do this, they are embedded in paraffin, for example. This embedding in paraffin is usually done in so-called plastic cassettes, as are described in DE-43 33 118-A1, for example. To cut them, the embedded specimens are placed, together with the cassettes, in the clamp of a microtome.

A clamp which can hold cassettes of this type is known from U.S. Pat. No. 3,802,691. The clamp has a base part with fixed limit stops and forms, together with a movable clamping jaw, a holder for a cassette. Compression springs are provided between the clamping jaw and the base part. The first end of a pivotally mounted tie rod is connected to the clamping jaw via a thread, while its other end is connected to an eccentric. The clamping jaw can be adjusted slightly via the thread of the tie rod, so that the holder can be adapted to different cassette sizes.

A similarly constructed specimen clamp for a microtome is known from DE-36 07 766-C1. In this clamp, the tie rod is designed as a spindle on which the movable clamping jaw runs for the purpose of adjusting the holder size. In this case, the specimen is also clamped via an eccentric.

A quick-action chuck system for microtomes with a chuck head is known from DE-30 40 217-C2, in which the specimen can be clamped between four fingers forming a holder. The fingers are secured with cam followers, which are connected to one another by springs. The holder can be opened and closed via a pivot lever for the purpose of receiving the specimen.

A cassette clamp for a microtome is known, for example, from the publication "LEICA RM 2145" from Leica Instruments GmbH, July 1997. The cassette clamp has a base part with fixed limit stops as a support for the paraffin cassette. Provided opposite these limit stops there is a clamping jaw which is mounted on the base part so as to pivot about an axis. The clamping jaw is pre-stressed via a tension spring and thus presses against the inserted cassette. Also arranged on the clamping jaw there is a lever via which the clamping jaw can be moved about its pivot axis into a cassette-exchange position counter to the spring force.

In these known cassette clamps, two hands are needed to change cassettes. One hand is used to move the lever into the cassette-exchange position and to hold it there counter to the spring force. The cassette is then either removed or inserted using the other hand. When holding the lever in the cassette-exchange position, force has to be applied, so that there is a danger of slipping and injuring oneself on the cutting knife.

BRIEF SUMMARY OF THE INVENTION

It is therefore an object of the present invention to simplify the cassette exchange in the specimen holder of a microtome and in so doing to minimize the force applied.

A pivot lever, according to preferred embodiments of the present invention, locks in the cassette-exchange position and therefore no longer needs to be held. The pivot lever is connected to a spring and is mounted on the base part via a pivot axis provided between the first and second ends of the spring. The pivot lever forms, together with the spring, a tilting clamp mechanism. By simply inserting the cassette into this opened holder, the tilting clamp mechanism is activated and the cassette is held in the holder between the limit stops and the clamping jaw. The clamp is opened by moving the pivot lever across a pressure point. Thereafter, the pivot lever is moved onward into the cassette-exchange position by the spring.

The spring according to preferred embodiments of the present invention performs a an over-center function wherein the magnitude of the spring bias changes at different pivotal positions of the pivot lever with respect to the base portion. The spring bias is relatively smaller when the pivot lever is in the cassette-clamping and cassette-exchange positions, and the spring bias is relatively larger in a transitional center position between the cassette-clamping and cassette-exchange positions. According to most preferred embodiments of the present invention, the transitional center position occurs when the longitudinal axis of the spring intersects the pivot axis of the pivot lever. Thus, the pivot lever according to preferred embodiments of the present invention tends to remain in one of the cassette-clamping and cassette-exchange positions, and tends to resist crossing the transitional center position between the cassette-clamping and cassette-exchange positions.

The objects of the present invention are achieved by a clamp for holding a specimen cassette with respect to a microtome. The clamp comprises a base including at least one fixed limit stop adapted for restraining the specimen cassette; a lever pivotally mounted with respect to the base, the lever pivoting on an axis; a jaw adapted for clamping the specimen cassette with respect to the at least one fixed limit stop, the lever supporting the jaw for movement around the axis; and a spring extending from a first end engaging the base to a second end engaging the lever, the spring exerting a biasing force on the lever and the base. Wherein the biasing force reaches a maximum when the axis intersects a line between the first and second ends.

The objects of the present invention are also achieved by a cassette clamp for a microtome cassette. The cassette clamp comprises a base part having at least one fixed limit stop adapted for receiving the cassette, at least one pivotally mounted clamping jaw, and a spring; the limit stops and the clamping jaw being adapted for clamping the cassette therebetween by spring force, the clamping jaw being connected to a pivot lever and being able to move counter to the spring force from a cassette-clamping position into a cassette-exchange position via the pivot lever, wherein a first end of the spring engages the base part and a second end of the spring engages the pivot lever, the pivot lever being mounted on the base part via a pivot axis arranged between the first end of the spring and the second end of the spring, wherein the pivot lever and the spring form a tilting clamp mechanism adapted to be activated by installing the cassette in the cassette-exchange position.

BRIEF DESCRIPTION OF THE DRAWINGS

A cassette clamp according to the present invention is explained in greater detail on the basis of an illustrative embodiment and with the reference to the diagrammatic illustrations in which.

DETAILED DESCRIPTION OF THE INVENTION

Figure 1:
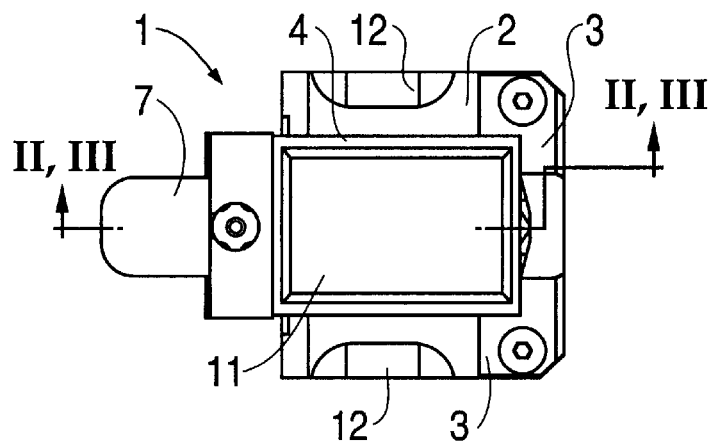
FIG. 1 shows a view of the specimen clamp.

FIG. 1 shows a view of the specimen clamp 1 for a microtome, with a base part 2 and with limit stops 3 formed integrally thereon. Provided opposite the limit stops 3 there is a clamping jaw 5 on a pivot lever 7. A cassette 4 with the specimen 11 which is to be cut is arranged between the limit stops 3 and the clamping jaw 5. In addition, the specimen clamp 1 has two recesses 12 lying opposite each other on the base part 2. These recesses 12 permit secure gripping of the cassette 4 when it is being changed.

Figure 2:
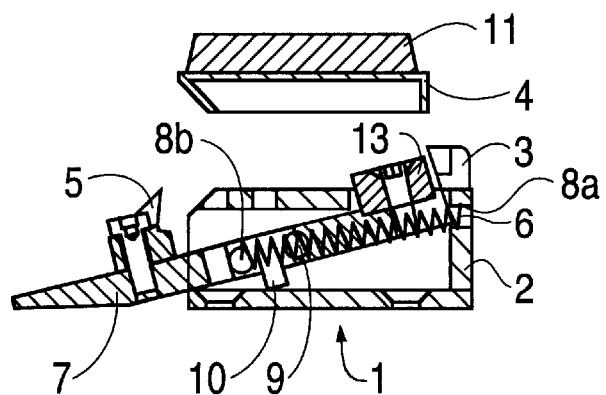
FIG. 2 shows a cross section along the line II—II of the specimen clamp in the cassette-exchange position.

FIG. 2 shows a section along the line II—II in FIG. 1. The cassette clamp 1 shown here is located in the cassette-exchange position.

The pivot lever 7 is mounted on the base part 2 so as to pivot about a pivot axis 9. A spring 6 is secured with its first end 8a on the base part 2 and with its second end 8b on the pivot lever 7. The clamping jaw 5 is arranged on the pivot lever 7. In the illustrative embodiment shown here, this jaw 5 is arranged to be longitudinally displaceable on the pivot lever 7, in order also to hold different sizes of cassettes 4 securely. An adjustable movement limiter 10 is also screwed onto the pivot lever 7 and has the object of limiting the range of pivoting of the lever 7 in the cassette-exchange position.

A trigger mechanism 13 is secured on the pivot lever 7, opposite the clamping jaw 5. Upon insertion of the cassette 4 into the cassette clamp 1, the trigger mechanism 13 and thus the pivot lever 7 are pressed down by the cassette 4. The lever 7 turns about its pivot axis 9. By means of the arrangement of the pivot axis 9 between the first end 8a and the second end 8b of the spring 6, the spring 6 is first tensioned by the downward movement of the trigger 13. The spring tension reaches a maximum when the longitudinal axis of the spring 6 intersects the pivot axis 9. When this pivot axis 9 is passed, the spring tension relaxes again and the pivot lever 7 is biased downward by the spring force.

When inserting the cassette 4, only the maximum spring tension needs to be overcome. The spring 6 is then relaxed once again and the lever 7 is biased downward. The tilting clamp mechanism thus obtained allows the cassette 4 to be clamped with just one hand. Thus, the resiliently prestressed pivot lever 7 no longer needs to be held by hand in the exchange position while the other hand is bringing the cassette into position.

Figure 3:
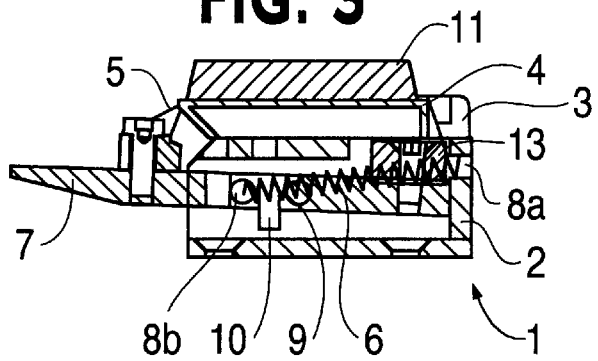
FIG. 3 shows a cross section along the line III—III of the specimen clamp in the cassette-clamping position.

FIG. 3 shows a cross section along the line III—III in FIG. 1. The cassette clamp 1 shown here is located in the cassette-clamping position. The cassette 4 with the specimen 11 to be cut is held between the clamping jaw 5 and the fixed limit stops 3.

In contrast to FIG. 2, the spring 6 is situated above the pivot axis 9. By pressing the pivot lever 7 down, the latter turns about its axis 9 and the spring 6 is tensioned. When the longitudinal axis of the spring 6 intersects the pivot axis 9, the maximum spring tensioning is reached. When this point is passed, the spring tension relaxes again and the pivot lever 7 is biased downward into the cassette-exchange position by the spring force. In this position, the cassette 4 can be removed without applying any additional force to the cassette clamp 1.

An advantage achieved with the device according to the present invention is that when changing cassettes, no lever movement as a result of spring bias needs to be continuously opposed by one hand, and the clamping procedure is triggered directly by installing the cassette on the cassette clamp 1.

German Patent Application No. 198 16 375.4, filed Apr. 11, 1998, is hereby incorporated by reference in its entirety.

What is claimed is:

1. A clamp for holding a specimen cassette with respect to a microtome, the clamp comprising:

a base including at least one fixed limit stop adapted for restraining the specimen cassette;

a lever pivotally mounted with respect to said base, said lever pivoting on an axis;

a jaw adapted for clamping the specimen cassette with respect to said at least one fixed limit stop, said lever supporting said jaw for movement around said axis;

a spring extending from a first end engaging said base to a second end engaging said lever, said spring exerting a biasing force on said lever and said base;

wherein said biasing force reaches a maximum when said axis intersects a line between said first and second ends; and a trigger adapted for pivoting said lever to a specimen cassette clamping position, said trigger being mounted on said lever.

2. The clamp according to claim 1, further comprising:

an adjustable movement limiter arranged between said base and said lever.

3. The clamp according to claim 1, wherein said jaw is adjustably positioned with respect to said lever, said jaw being adapted to adjust for different size specimen cassettes.

* * * * *